United States Patent [19]

Ashby

[11] 4,447,369

[45] May 8, 1984

[54] ORGANOMAGNESIUM COMPOUNDS

[75] Inventor: Eugene C. Ashby, Atlanta, Ga.

[73] Assignee: Ethyl Corporation, Richmond, Va.

[21] Appl. No.: 488,080

[22] Filed: Apr. 25, 1983

Related U.S. Application Data

[63] Continuation-in-part of Ser. No. 369,340, Apr. 16, 1982, abandoned, which is a continuation-in-part of Ser. No. 303,404, Sep. 18, 1981, abandoned.

[51] Int. Cl.$^3$ .............................................. C07F 3/02
[52] U.S. Cl. ................................. 260/665 R; 502/152
[58] Field of Search ................. 260/665 R; 252/431 R

[56] References Cited

U.S. PATENT DOCUMENTS

| | | | |
|---|---|---|---|
| 3,306,917 | 2/1967 | Shapiro et al. | 260/665 R X |
| 3,405,186 | 10/1968 | Davey et al. | 260/665 R |
| 3,641,186 | 2/1972 | Shepherd | 260/665 R |
| 3,646,231 | 2/1972 | Kamienski et al. | 260/665 R |
| 3,766,280 | 10/1973 | Kamienski et al. | 260/665 R |
| 4,069,267 | 1/1978 | Kamienski et al. | 260/665 R |
| 4,127,507 | 11/1978 | Fannin et al. | 260/665 R X |
| 4,207,207 | 6/1980 | Sanchez et al. | 260/665 R X |
| 4,222,969 | 9/1980 | Fannin et al. | 260/665 R |
| 4,299,781 | 11/1981 | Fannin et al. | 260/665 R |
| 4,325,840 | 4/1982 | Malpass | 260/665 R |
| 4,329,301 | 5/1982 | Bogdanovic | 260/665 R |

OTHER PUBLICATIONS

Glaze et al., J. of Organometallic Chem., vol. 5, p. 477 (1967).
Smith, J. of Organometallic Chem., vol. 64, p. 25 (1974).

*Primary Examiner*—Helen M. S. Sneed
*Attorney, Agent, or Firm*—Donald L. Johnson; John F. Sieberth; Paul H. Leonard

[57] ABSTRACT

A method of effectively increasing the settling rate of solid co-products from relatively viscous dialkyl magnesium solutions and thereby reducing the viscosity of such solutions wherein a small quantity of bis(cyclopentadienyl)magnesium or other cyclopentadienyl compound is added thereto. Alternatively, the bis(cyclopentadienyl)magnesium may be prepared in situ by adding cyclopentadiene directly to the dialkyl magnesium.

25 Claims, No Drawings

ORGANOMAGNESIUM COMPOUNDS

CROSS REFERENCE TO RELATED APPLICATIONS

This is a continuation-in-part of application Ser. No. 369,340, filed Apr. 16, 1982, now abandoned, which in turn is a continuation-in-part of application Ser. No. 303,404 filed Sept. 18, 1981, now abandoned.

BACKGROUND OF THE INVENTION

The present invention is in the general field of organomagnesium compounds and relates in particular to dialkylmagnesium compounds and cyclopentadienyl magnesium compounds. The invention especially relates to di-n-hexylmagnesium and bis(cyclopentadienyl)magnesium.

Diorganomagnesium compounds are well known for their usefulness in a wide variety of chemical reactions. As reagents, these compounds can be used for the alkylation of ketones and the alkylation of metal halides or oxides to the corresponding metal alkyls. As catalysts, diorganomagnesium compounds are useful in the dimerization and polymerization of olefins, see Great Britain Pat. No. 1,251,177, the polymerization of epoxides, see U.S. Pat. No. 3,444,102, and the preparation of telomers, see U.S. Pat. No. 3,742,077. While they perform many of the same types of functions performed by Grignard reagents, diorganomagnesium compounds, owing to differences in electronic and steric factors, are more reactive than Grignard reagents toward certain types of compounds. In general, see also U.S. Pat. Nos. 3,646,231 and 3,822,219.

The utility of diorganomagnesium compounds is lessened by the fact that many are either solids or highly viscous liquids. This problem is generally overcome either by dissolving the compound in an inert hydrocarbon solvent (where possible) or by solvating the compound. All are unstable upon exposure to moisture and air and require handling under an inert atmosphere. Some diorganomagnesium compounds, with straight chain lower alkyl groups of up to four carbon atoms, are insoluble by themselves in hydrocarbon solvents and thus require solubilizing agents which will form a soluble complex. Examples of such solubilizing agents are alkyllithium compounds, see U.S. Pat. No. 3,742,077, dialkyl zinc compounds, see U.S. Pat. No. 3,444,102, alkali metal hydrides, see U.S. Pat. No. 3,655,790, and organoaluminum compounds, see U.S. Pat. Nos. 3,737,393 and 3,028,319, and combination of certain dialkylmagnesium compounds in hydrocarbon solvents. See U.S. Pat. Nos. 4,069,267 ($C_1$ to $C_4$ di-n-alkylmagnesium and $C_6$ to $C_{18}$ dialkylmagnesium), 4,127,507 (di-n-butylmagnesium and diethylmagnesium), 4,207,207 (dimethylmagnesium and di-n-butylmagnesium).

Processes for the preparation of dialkylmagnesium compounds are disclosed in U.S. Pat. No. 3,737,393. Processes for the preparation of bis(alkenyl)magnesium compounds are disclosed in U.S. Pat. No. 3,641,186.

U.S. Pat. Nos. 2,788,377 and 2,993,537 disclose the preparation of bis(cyclopentadienyl)magnesium or mixtures of bis(cyclopentadienyl)magnesium and bis(methyl-, or other lower alkylcyclopentadienyl)magnesium by direct reaction of cyclopentadiene or methylcyclopentadiene with metallic magnesium at high temperatures.

Dialkyl magnesium compounds have been prepared by the reaction of an alkyl halide with magnesium in an ether medium, followed by the addition of dioxane. Magnesium compounds obtained from such a process cannot be completely freed of ether. Since ether may have an adverse effect in certain applications for the dialkyl magnesium compounds, particularly as a catalyst component in Ziegler-Natta polymerization processes, such a process has major disadvantages.

When the foregoing reaction is conducted in an ether-free dispersion medium, such as in a hydrocarbon medium, the organomagnesium compounds are sometimes obtained as a precipitate having about the gross composition of organomagnesium halides. Such insoluble organomagnesium compounds are not only difficult to handle, but pose a number of problems for use in a polymerization process. Even when a dialkyl magnesium compound is prepared which is soluble in the hydrocarbon medium, the resulting solution is highly viscous, having a consistency similar to molasses in January.

The insolubility of the lower alkyl magnesium compounds makes preparation of them in a form free of undesirable co-product magnesium halides difficult. In particular the direct reaction of magnesium metal with an organic halide is disclosed in Glaze and Selman, *Journal of Organometallic Chemistry*, Vol. 5. p. 477 (1967), and W. N. Smith, *Journal of Organometallic Chemistry*, Vol. 64, p. 25 (1974). These articles deal with the preparation of diorganomagnesium compounds with straight chain alkyl groups of 5 carbon atoms and higher. Such compounds are soluble in hydrocarbon solvents and thus readily separable from the concurrently produced magnesium halide and unreacted magnesium.

In one process for making di-n-hexylmagnesium, magnesium powder and hexyl chloride are reacted in a hydrocarbon solvent in the presence of recycled di-n-hexylmagnesium as an activator. The reaction mixture is a viscous slurry of di-n-hexylmagnesium dissolved in hexane containing suspended magnesium powder and by-product magnesium chloride. The addition of a small amount of an aluminum compound such as diisobutylaluminum hydride, triethylaluminum or aluminum isopropoxide renders the solution more fluid or less viscous. The aluminum alkyl compound may also be added to the starting reaction mixture with similar viscosity reducing results. Although not wishing to be bound by any particular theory, it is believed that the aluminum compound causes partial depolymerization of long chains of associated magnesium dialkyls thus reducing viscosity. Since the magnesium product then contains a significant amount of aluminum, it is undesirable for some uses.

The basic reaction for preparing di-n-hexylmagnesium from an alkyl halide and magnesium is illustrated by the following equation:

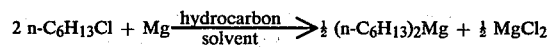

$$2\ n\text{-}C_6H_{13}Cl\ +\ Mg \xrightarrow[\text{solvent}]{\text{hydrocarbon}} \tfrac{1}{2}\ (n\text{-}C_6H_{13})_2Mg\ +\ \tfrac{1}{2}\ MgCl_2$$

The di-n-hexylmagnesium is soluble in the hydrocarbon solvent, but the solution is extremely viscous. The magnesium chloride is a fine insoluble powder and is dispersed throughout the solution. Additionally, excess magnesium powder is dispersed in the solution. It is necessary to remove these solids from the magnesium alkyl product. The settling rate for such solids is extremely slow and consequently the viscosity remains high. Observation of untreated solution left standing for several days disclosed little or no settling. Heating of the solution provides some reduction in viscosity, but not enough for practical purposes. An additive is thus essential to provide a rapid settling rate and thereby increase the fluidity of such solution.

Accordingly there exists a need for an effective way of increasing the settling rate of solids formed on reacting alkyl halides with magnesium to form dialkylmagnesium compounds. Another desirable contribution would be a way of reducing the viscosity of normally viscous hydrocarbon solutions of dialkylmagnesium compounds without diluting the solutions to any significant extent, and without recourse to use of complexing ethers or the like. Still another desirable contribution would be a way of improving the solubility of dialkylmagnesium compounds in non-complexing solvents, especially in hydrocarbons.

SUMMARY OF THE INVENTION

One aspect of this invention involves providing a process for increasing the settling rate of an initially viscous dialkylmagnesium solution containing fine solids dispersed therein. In a process for producing dialkylmagnesium having the same or different alkyl groups wherein magnesium and an alkyl halogenide or mixture of alkyl halogenides are reacted in an inert, ether-free dispersion medium, the process is improved by adding a relatively small amount of a cyclopentadiene compound to the reaction mixture whereby the settling rate of the solid co-product from the dialkylmagnesium solution is effectively increased.

Another embodiment of this invention relates to the provision of solutions of dialkylmagnesium compounds in noncomplexing solvents, especially hydrocarbons, having reduced viscosities. This is achieved by adding to the viscous dialkylmagnesium solution a relatively small quantity of a cyclopentadiene compound, such as cyclopentadiene or a hydrocarbon substituted cyclopentadiene, or a bis(cyclopentadienyl)magnesium compound derived therefrom.

Still another embodiment of this invention relates to the provision of a composition of matter comprising a liquid hydrocarbon solvent, a dialkylmagnesium compound normally relatively insoluble in said solvent, and a small amount of a cyclopentadienyl magnesium moiety which effectively increases the solubility of said dialkylmagnesium compound in said solvent.

DESCRIPTION OF THE PREFERRED EMBODIMENTS

In general, a small quantity of a cyclopentadiene compound, preferably bis(cyclopentadienyl)magnesium, or cyclopentadiene is added to a viscous solution of a dialkyl magnesium, especially di-n-hexylmagnesium, to substantially increase the settling rate of solids in the solution which is evidence of a reduced viscosity of the di-n-hexylmagnesium solution. The cyclopentadiene compound may also be added to a reaction mixture from which the dialkylmagnesium solution is obtained.

The present invention includes the use of cyclopentadiene, hydrocarbon substituted cyclopentadienes and the bis(cyclopentadienyl)magnesium compounds derived therefrom.

Although not wishing to be bound by any particular theory, the bis(cyclopentadienyl)magnesium compound is believed to redistribute readily with highly oligomerized dialkylmagnesium compounds to form lower oligomer RMgR' compounds, and thereby form less viscous hydrocarbon solutions. It is also believed that the addition of the cyclopentadiene hydrocarbon results in the formation in situ of cyclopentadienylmagnesium species which likewise cause the formation of lower oligomer RMgR' compounds by interaction with the more highly oligomerized dialkylmagnesium compounds.

Some examples of the cyclopentadiene hydrocarbons are cyclopentadiene, indene, and fluorene (alpha-diphenylenemethane), and the various ring substituted derivatives thereof, such as methylcyclopentadiene, dimethylcyclopentadiene, trimethylcyclopentadiene, diethylcyclopentadiene, butylcyclopentadiene, phenylcyclopentadiene, cyclopropylcarbinylcyclopentadiene, 1-methylfluorene, and the like. Various mixtures of such cyclopentadiene hydrocarbons may also be used. Cyclopentadiene may be obtained from coal tar or as a co-product from the manufacture of ethylene. Indene is obtained from the fraction of coal tar distilleries which boils from 176°–182° C. Fluorene is derived from coal tar or by reduction of diphenylene ketone with zinc. In general, the monocyclic cyclopentadiene hydrocarbons are illustrated by the following formula:

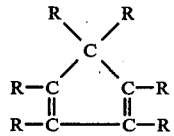

wherein each R is, independently, hydrogen or a hydrocarbon substituent such as an alkyl group (preferably containing up to about 4 carbon atoms, most preferably methyl), a cycloalkyl group, or an aryl group (preferably phenyl or alkyl substituted phenyl wherein each alkyl group contains up to about 4 carbon atoms). For best results, the cyclopentadiene hydrocarbons should be added to the dialkylmagnesium dispersion or solution in substantially monomeric form. Thus cyclopentadiene itself and its lower alkyl derivatives which tend to exist in dimeric form at ordinary temperatures are preferably subjected to suitable elevated temperatures to cause the formation of the monomeric species just prior to their use.

The cyclopentadienyl magnesium compounds which may be employed in the practice of this invention may be represented by the general formula:

$R_2Mg$ wherein R is a hydrocarbon group having from 5 to 17 carbon atoms which embodies a group of 5 carbons having the general configuration found in cyclopentadiene.

A few exemplary bis(cyclopentadienyl)magnesium compounds which may be utilized in the practice of this invention include:
bis(cyclopentadienyl)magnesium
bis(methylcyclopentadienyl)magnesium
bis(dimethylcyclopentadienyl)magnesium
bis(trimethylcyclopentadienyl)magnesium
bis(ethylcyclopentadienyl)magnesium
bis(butylcyclopentadienyl)magnesium bis(indenyl)magnesium
bis(methylindenyl)magnesium
bis(fluorenyl)magnesium
bis(methylfluorenyl)magnesium Bis(cyclopentadienyl)magnesium (and its analogs) may be prepared directly from the appropriate cyclopentadiene hydrocarbon (cyclopentadiene, methylcyclopentadiene, diethylcyclopentadiene, indene, fluorene, etc.) and magnesium metal as is illustrated by the following equation for the preparation of bis(cyclopentadienyl)magnesium:

$$2C_5H_6 + Mg \rightarrow (C_5H_5)_2Mg + H_2$$

The instant invention is suitable for use with all hydrocarbon soluble dialkylmagnesium compounds. Examples of such compounds are methylbutylmagnesium, ethylbutylmagnesium, ethylhexylmagnesium, dibutylmagnesium, di-n-hexylmagnesium, di-n-octylmagnesium, octyldecylmagnesium and butyloctylmagnesium, dipropylmagnesium, diisopropylmagnesium, di-n-amylmagnesium, and mixtures of these compounds.

Remotely branched alkyl magnesium compounds, i.e., compounds in which the alkyl groups each contain at least 5 carbon atoms with branching occurring at least 3 carbon atoms from the magnesium atom, which tend to have good hydrocarbon solubility, are further improved pursuant to this invention, especially from the standpoint of reduced viscosity.

Suitable hydrocarbon solvents or ether-free liquid dispersive mediums include paraffinic hydrocarbons such as the various isomers of pentane, hexane, heptane, octane, nonane, decane, dodecane, and the like, as well as mixtures such as paraffinic gasoline fractions, or other petroleum fractions; cycloparaffinic hydrocarbons such as cyclopentane, methylcyclopentane, cyclohexane, methylcyclohexane, and the like; and aromatic hydrocarbons, such as benzene, toluene, xylene, 1,2,3,4-tetrahydronapthalene, ethylbenzene, and the like. Mixtures of such liquid dispersion media may also be used. Saturated aliphatic and saturated cycloaliphatic hydrocarbons having 5 to 20 carbon atoms and mononuclear aromatic hydrocarbons having 6 to 20 carbon atoms are preferred. Especially preferred are the straight and branched chain alkane hydrocarbons, the cycloalkane and alkyl-substituted cycloalkane hydrocarbons, and benzene and the alkyl benzenes, having up to about 15 carbon atoms.

Preferred alkyl halogenides for preparing the dialkyl magnesium compounds are primary alkyl halogenides or their mixtures. These will generally have 1 to about 25 carbon atoms in the molecule, the methyl, ethyl, butyl, heptyl, octyl, decyl, dodecyl, hexadecyl, octadecyl, and eicosyl halogenides being exemplary. For economy reasons, chlorides are conveniently used, but bromides, iodides or mixtures of these halogenides may be used, as desired. The term "alkyl halogenides" includes aralkyl halogenides, for instance, 3-chloro-n-propyl benzene.

Metallic magnesium is preferably employed in a finely divided state, usually as a powder with a particle size less than 50 mesh (U.S. Series). With such fine particle size, activation of the metal is effective in giving good yields. Other forms of magnesium such as shavings and ribbons normally give very poor yields.

The reaction between the metallic magnesium and the alkyl halogenide should be between 30° C. and 200° C., and preferably between 50° C. and 150° C. The pressure may vary between wide limits, and is not critical, but should be sufficiently high that the reaction medium and the reactants are substantially in the liquid state. The reaction may be carried out at atmospheric or other pressures and is normally done in a sealed reactor to avoid reactant losses and contamination of product. Pressures as high as 40 to 50 psig have been used without adverse results.

It is preferable to add the bis(cyclopentadienyl)magnesium compound or the cyclopentadiene hydrocarbon near the end of the reaction, but any of these compounds may be added at the beginning of or during the reaction. The temperature of addition after reaction is completed is preferably about 20°–120° C.

The amount of bis(cyclopentadienyl)magnesium compound necessary to be added to the dialkylmagnesium solution to increase the settling rate or to reduce the viscosity of the system may be varied considerably. Based on the amount of dialkylmagnesium in the solution, amounts of the bis(cyclopentadienyl)magnesium compound may range from about 0.05 mole percent to about 50 mole percent. Amounts of about 2 mole percent and 11 mole percent have been found to be effective. In general, the amount of bis(cyclopentadienyl)magnesium (or other cyclopentadienyl magnesium compound) added or used should be sufficient to provide a desired settling rate or viscosity. In addition, the amount added or used should be kept as small as will accomplish the desired objective. Greater amounts may be added of course, but no particular benefit is seen to accrue thereby.

The reaction should be carried out under an inert gas blanket, generally a nitrogen blanket.

The process often results in a relatively thick slurry, so that agitation is essential. Ordinary stirring is usually adequate.

The invention will be more readily understood by references to the following examples. Such examples are merely illustrative and are not to be construed as limiting the scope of the invention.

GENERAL PROCEDURE

The reactions were carried out in a round bottom, 4-necked, 500 cc flask under a nitrogen atmosphere. The flask was fitted with a thermometer, condenser and Cruciform stirrer. The flask and contents were heated with stirring to 97°–99° C. and maintained at such temperatures while slowly adding 1-chlorohexane (dried over molecular sieves). Heating was then continued for a desired period. The reaction mass was transferred to a 250 mL stoppered graduated cylinder for settling rate measurements.

Settling rate measurements were made at room temperature at various intervals of time with the heights of the clear phases and the heights of the solids phases measured in inches.

Following the foregoing procedure, the ensuing specific examples were recorded. In this connection, Examples 3 and 4 are comparative examples in the sense that they illustrate the state of the art prior to the advent of this invention.

EXAMPLE 1

To the flask were charged 69 grams of n-heptane, 6.4 grams of magnesium powder, 5 cc of di-n-hexylmagnesium solution and 1.8 grams of bis(cyclopentadienyl)magnesium. While maintaining the temperature at 97°–98° C., 32 grams of 1-chlorohexane was added over a period of 2.5 hours. Additional heating time was 33 minutes. Settling rate measurements are shown in Table I.

EXAMPLE 2

To the flask were charged 138 grams of n-heptane, 12.8 grams of magnesium powder, 10 cc in di-n-hexylmagnesium solution. Heating was to 98° C. Over a period of two hours, 64 grams of 1-chlorohexane was added. The reaction mass was quite viscous when approximately one-half of the hexyl chloride had been added. After addition, heating was continued for 13 minutes and 1.0 cc of cyclopentadiene was added. A viscous reaction mass foamed up into the condensers and then quickly subsided. The reaction mass was fluid, much less viscous. Settling rate measurements are shown in Table I.

EXAMPLE 3

To the flask were charged 138 grams n-heptane, 12.8 grams magnesium powder, 10 cc of di-n-hexylmagnesium solution, and 1.1 grams of solid, anhydrous aluminum isopropoxide. Heating was to 98° C. Afterwards 64 grams of 1-chlorohexane was added over a period of 75 minutes. Additional heating time was 15 minutes. Most of the reaction mass was transferred to the cylinder for settling rate measurements. The results of these measurements are shown in Table I.

EXAMPLE 4

Using a typical commercial-type recipe, to the flask were charged 1725 grams of n-heptane, 160 grams of magnesium powder, 13.8 grams of solid anhydrous aluminum isopropoxide, and 100–200 cc heel or residue of di-n-hexylmagnesium solution from a previous run. Afterwards, 800 grams of 1-chlorohexane was added via an FMI pump over a period of 214 minutes. Additional heating time was 30 minutes at a temperature of 97°–99° C. Settling rate measurements are shown in Table I.

EXAMPLE 5

A one-liter straight-wall jacketed reactor was charged with 46.7 grams of 100 mesh Reade magnesium powder in 540 mL of dry heptane. The reactor was equipped with a thermometer, mechanical stirrer, ice cooled condenser and a 250 mL addition funnel. To the charge was added 30 mL of ethylbutylhexylmagnesium in heptane (2.84 weight percent magnesium and 0.11 weight percent aluminum). The mixture was heated under the ice cooled reflux condenser to reflux. The addition funnel was charged with 100 mL of heptane, 74.2 grams (1.15 mole) of ethyl chloride, 24.0 mL (0.23 mole) of butyl chloride and 48 mL (0.35 mole) of hexyl chloride. The alkyl chloride mixture was added dropwise. After two hours and after which about two-thirds of the chloride had been added, the mixture became very viscous and stirring became difficult. Three milliliters of (0.036 mole) of freshly distilled cyclopentadiene was added and the viscous mixture immediately became about as fluid as heptane. Addition of the alkyl chloride was continued. The reaction appeared slower as the reflux temperature dropped to 91° C. When addition of the chloride was completed, continued refluxing brought the temperature back to 97°–98° C. The mixture was cooled and settling followed. Another three milliliters (0.036 mole) of cyclopentadiene were added. As reflected in Table II, settling rate measurements were taken at 90° C., 80° C. and 70° C., respectively, and at one minute intervals. The solids containing phase continually decreased. The 70° C. solution was decanted into a flask, giving a clear fluid. After standing overnight, the ethylbutylhexylmagnesium solution was cloudy and a precipitate was present on the walls of the flask. A sample ethylbutylhexylmagnesium product having an ethyl/butyl/hexyl ratio of 5/1/1.5 was decanted and analyzed and found to contain 1.88 weight percent magnesium (49 percent yield). The solids portion was isolated by filtration and titration with heptane. Analysis of about 3.3 grams showed 6.6 weight percent magnesium and 4.12 weight percent chloride indicating that 21.5 percent of the magnesium was as magnesium chloride.

TABLE I

Settling Rate Measurements

| | | Time Interval (minutes) | | | | | | |
|---|---|---|---|---|---|---|---|---|
| | | 60 | 120 | 180 | 240 | 300 | 390 | Overnight |
| Ex. 1 | | | | | | | | |
| Height (Inches) | Clear Phase | 1¼ | 2⅞* | 3½ | 3¾ | 3⅞ | — | — |
| | Solids Phase | 4½ | 2¾* | 2¼ | 2 | 1⅞ | — | — |
| Ex. 2 | | | | | | | | |
| Height (Inches) | Clear Phase | 2¼ | 4½ | 6½ | 7⅜ | 7⅜ | — | 8¾ |
| | Solids Phase | 9¼ | 7 | 5⅝ | 4½ | 3⅞ | — | 3⅛ |
| Ex. 3 | | | | | | | | |
| Height (Inches) | Clear Phase | 1⅛ | 2⅛ | 3¼ | 3⅞ | 4¾ | — | 8¼ |
| | Solids Phase | 10⅛ | 9⅛ | 7⅞ | 7¼ | 6⅜ | — | 3 |
| Ex. 4 | | | | | | | | |
| Height (Inches) | Clear Phase | 1 | 2¾* | — | 4** | 6 | 7⅜ | 7½ |
| | Solids Phase | 9 | 7¼* | — | 6** | 4 | 2⅝ | 2½ |

*Interval at 150 minutes.
**Interval at 210 minutes.

TABLE II

Settling Rate Measurements
Height in Centimeters of Solids-Containing Phase of Example 5

| Time (Minutes) | At 90° C. | At 80° | At 70° C. |
|---|---|---|---|
| 0 | 20.5 (880)* | 20.3 (870)* | 20.0 (860)* |
| 1 | 18.4 | 18.4 | 18.4 |
| 2 | 16.6 | 16.8 | 17.0 |
| 3 | 14.7 | 15.1 | 15.5 |
| 4 | 12.8 | 13.5 | 14.0 |
| 5 | 11.0 | 11.9 | 12.6 |
| 6 | 9.7 | 10.4 | 11.2 |
| 7 | 8.9 | 9.4 | 10.0 |
| 8 | 8.3 (340)* | 8.8 | 9.3 |
| 9 | 8.1 | 8.4 | 8.8 |
| 10 | 7.8 | 8.1 | 8.4 |
| 11 | 7.6 | 7.9 | 8.1 |
| 12 | 7.5 (300)* | — | 7.9 |

TABLE II-continued

Settling Rate Measurements
Height in Centimeters of Solids-Containing Phase of Example 5

| Time (Minutes) | At 90° C. | At 80° | At 70° C. |
|---|---|---|---|
| 13 | — | 7.5 | — |
| 14 | — | — | 7.5 |
| 15 | — | 7.3 | — |
| 16 | — | — | 7.3 |
| 18 | — | 7.1 | 7.1 |
| 20 | — | 7.1 | 7.0 |
| 24 | — | — | 6.9 |

*Figures in parenthesis are approximate volumes of solids-containing phase in milliliters.

EXAMPLE 6

Using the apparatus and procedures of Example 5, an ethylbutylhexylmagnesium product having an ethyl/butyl/hexyl ratio of 5/1/2.4 was produced. The reactor was charged with 36.1 grams of magnesium and 400 milliliters of heptane. Thirty milliliters of ethylbutylhexylmagnesium from Example 5 was added to the charge. The mixture was then heated to 98° C. and to such was added a mixture of 100 milliliters of heptane, 52.2 grams (0.81 mole) of ethyl chloride, 16.7 milliliters (0.16 mole) of butyl chloride, and 52 milliliters (0.38 mole) of hexyl chloride. The chloride mixture was added over a period of three and one-quarter hours at a temperature of 96°–98° C. under a dry ice condenser. Stirring was continued for 20 minutes after which 1.7 milliliters (1.4 grams or 21 millimoles) of dry cyclopentadiene was added dropwise via syringe. Stirring was continued another ten minutes after which the mixture settled and was decanted giving a yellowish-green clear solution. On cooling, the solution turned milky. After standing overnight, a considerable amount of solid was seen in the solution. Part of the liquid, about 200 milliliters was separated for analysis, and the remainder was returned to the reaction flask. Analysis showed the liquid product to contain 2.32 weight percent magnesium. Three milliliters of dibutylaluminum hydride was added to the remainder at 75° C. and stirred for one-half hour. After settling, the liquid was decanted and analyzed. Analysis showed 2.23 weight percent magnesium.

From the latter, it is readily seen that substantially no undissolved magnesium remained and that cyclopentadiene is an effective solubilizer, viscosity reducer, or fluidity enhancer.

The compositions of this invention are useful in various known applications for dialkylmagnesium compounds. By virtue of their reduced viscosity and enhanced solubility, the solutions are more readily usable than the more viscous and less concentrated solutions existing absent the cyclopentadienylmagnesium or cyclopentadiene hydrocarbon additives of this invention. Thus, for example, the dialkylmagnesium solutions of this invention such as hydrocarbon solutions of di-n-hexylmagnesium are useful in forming catalyst systems for polymerization of olefins such as ethylene and propylene.

The foregoing disclosure and description of the invention is illustrative and explanatory thereof and various changes in the illustrated process may be made within the scope of the appended claims without departing from the spirit of the invention.

What is claimed is:

1. In a process for producing dialkylmagnesium having the same or different alkyl groups wherein magnesium and an alkyl halogenide or mixture of alkyl halogenides are reacted in an inert, ether-free dispersion medium, the improvement therein comprising the step of adding a relatively small amount of a cyclopentadiene compound to the reaction mixture whereby the settling rate of the solid co-product from the dialkylmagnesium solution is effectively increased.

2. The process of claim 1 wherein the cyclopentadiene compound is added at the beginning of the reaction, during the reaction or after the reaction is complete.

3. The process of claim 1 wherein the cyclopentadiene compound is added near the end of the reaction.

4. The process of claim 1 wherein the cyclopentadiene compound is cyclopentadiene or a lower alkyl substituted cyclopentadiene hydrocarbon added in substantially monomeric form.

5. The process of claim 1 wherein the cyclopentadiene compound is selected from the group consisting of cyclopentadiene, methylcyclopentadiene, indene, fluorene or mixtures thereof.

6. The process of claim 1 wherein the cyclopentadiene compound is a magnesium cyclopentadienide compound having the formula:

$$R_2Mg$$

wherein R is a hydrocarbon group having from 5 to 17 carbon atoms which embodies a group of 5 carbon atoms having the general configuration found in cyclopentadiene.

7. The process of claim 1 wherein the cyclopentadiene compound is bis(cyclopentadienyl)magnesium or a bis(cyclopentadienyl)magnesium compound in which the cyclopentadienyl group is substituted with at least one alkyl group having up to 4 carbon atoms.

8. The process of claim 1 wherein the dispersion medium is a hydrocarbon medium.

9. The process of claim 8 wherein the hydrocarbon medium is a paraffinic or cycloparaffinic hydrocarbon having from 5 to 20 carbon atoms or an aromatic hydrocarbon having from 6 to 20 carbon atoms.

10. The process of claim 8 wherein the hydrocarbon medium is an alkane, cycloalkane or mononuclear aromatic hydrocarbon having from 6 to 15 carbon atoms.

11. The process of claim 8 wherein the hydrocarbon medium consists essentially of one or more alkanes having from 5 to 10 carbon atoms.

12. The process of claim 1 wherein the dialkylmagnesium is hydrocarbon soluble and contains from 3 to 25 carbon atoms.

13. The process of claim 1 wherein the dialkylmagnesium being produced is selected from the group consisting of methylbutylmagnesium, ethylbutylmagnesium, ethylhexylmagnesium, di-n-hexylmagnesium, di-n-octylmagnesium and butyloctylmagnesium.

14. The process of claim 1 wherein the alkyl halogenide is an alkyl chloride having from 5 to 25 carbon atoms.

15. The process of claim 1 wherein the cyclopentadiene compound is added to a reaction mixture which is maintained at a temperature in the range of about 20° C. to about 120° C.

16. The process of claim 1 wherein the cyclopentadiene compound is added in an amount based on amount of dialkylmagnesium of about 0.05 mole percent to about 50 mole percent.

17. A composition of matter comprising a liquid hydrocarbon solvent, a dialkylmagnesium compound normally relatively insoluble in said solvent, and a small amount of a cyclopentadienyl magnesium moiety which effectively increases the solubility of said dialkylmagnesium compound in said solvent.

18. The composition of claim 17 wherein said cyclopentadienyl moiety is introduced into the composition as bis(cyclopentadienyl)magnesium.

19. The composition of claim 17 wherein said dialkylmagnesium compound is di-n-hexylmagnesium.

20. The composition of claim 17 wherein said hydrocarbon solvent is an alkane, cycloalkane or mononuclear aromatic hydrocarbon having from 6 to 15 carbon atoms.

21. The composition of claim 17 wherein said cyclopentadienyl magnesium moiety includes magnesium compounds derived from cyclopentadiene, methylcyclopentadiene, indene, fluorene or mixtures thereof.

22. The composition of claim 17 wherein said cyclopentadienyl magnesium moiety is introduced into the composition as a compound of the general formula:

$$R_2Mg$$

wherein R is a hydrocarbon group having from 5 to 17 carbon atoms which embodies a group of 5 carbons having the general configuration found in cyclopentadiene.

23. A composition of matter comprising a hydrocarbon solvent, a dialkylmagnesium compound which normally produces a highly viscous solution when mixed in said solvent, and a viscosity reducing effective amount of a cyclopentadienyl magnesium moiety thereby providing a substantially less viscous dialkylmagnesium-hydrocarbon solution.

24. The composition of claim 23 wherein said dialkylmagnesium compound is a hydrocarbon soluble dialkylmagnesium compound having at least five carbon atoms in the alkyl groups.

25. The composition of claim 23 wherein said cyclopentadienyl magnesium moiety is derived from a cyclopentadiene type compound having from 5 to 17 carbon atoms.

* * * * *